(12) United States Patent
Yoshida et al.

(10) Patent No.: US 9,221,045 B2
(45) Date of Patent: Dec. 29, 2015

(54) AUTOMATIC PREPARATION SYSTEM (71) Applicant: KABUSHIKI KAISHA YASKAWA DENKI, Kitakyushu-shi (JP)

(72) Inventors: Osamu Yoshida, Fukuoka (JP); Kohei Miyauchi, Fukuoka (JP)

(73) Assignee: KABUSHIKI KAISHA YASKAWA DENKI, Kitakyushu-Shi (JP)

( * ) Notice: Subject to any disclaimer, the term of this patent is extended or adjusted under 35 U.S.C. 154(b) by 0 days.

(21) Appl. No.: 14/133,658

(22) Filed: Dec. 19, 2013

(65) Prior Publication Data

US 2014/0178156 A1 Jun. 26, 2014

(30) Foreign Application Priority Data

Dec. 20, 2012 (JP) ................................. 2012-278569

(51) Int. Cl.
G01N 21/00 (2006.01)
B01L 1/02 (2006.01)
B25J 9/00 (2006.01)
B25J 21/00 (2006.01)
G01N 35/00 (2006.01)

(52) U.S. Cl.
CPC ............... B01L 1/025 (2013.01); B25J 9/0018 (2013.01); B25J 9/0084 (2013.01); B25J 21/00 (2013.01); G01N 35/0099 (2013.01)

(58) Field of Classification Search
CPC .......... A61J 1/00; B01L 1/025; G01N 35/099
See application file for complete search history.

(56) References Cited

U.S. PATENT DOCUMENTS 7,610,115 B2 * 10/2009 Rob et al. ...................... 700/245
8,931,999 B2 * 1/2015 Dorner et al. ................. 414/797

FOREIGN PATENT DOCUMENTS

| CN | 101501693 | 8/2009 |
|----|-----------|--------|
| EP | 2457550 | 5/2012 |
| EP | 2546032 | 1/2013 |
| EP | 2671687 | 12/2013 |
| JP | 61-76286 | 4/1986 |
| JP | 63-141341 | 6/1988 |
| JP | 2-273551 | 11/1990 |
| JP | 02-274484 | 11/1990 |
| JP | 05-220634 | 8/1993 |
| JP | 2000-176867 | 6/2000 |
| JP | 2000-237607 | 9/2000 |
| JP | 2000-356642 | 12/2000 |
| JP | 2003-269763 | 9/2003 |
| JP | 2006-043844 | 2/2006 |

(Continued)

OTHER PUBLICATIONS

Health Robotics: "CytoCare", Jul. 16, 2009, Retrieved from the Internet: URL:http://www.health-robotics.com/smartedit/downloads/en/cytocare7.pdf, XP055106148.

(Continued)

Primary Examiner — Jyoti Nagpaul
(74) Attorney, Agent, or Firm — Mori & Ward, LLP (57) ABSTRACT An automatic preparation system according to an embodiment includes a case, a pressure regulator, and a plurality of robots. The case has a workspace inside thereof. The pressure regulator keeps a negative pressure inside the case relative to the outside. The robots are installed on a ceiling surface of the case and have respective arms. The robots bring the arms into cooperation to perform a preparation operation.

20 Claims, 7 Drawing Sheets

(56) References Cited

FOREIGN PATENT DOCUMENTS

| | | |
|---|---|---|
| JP | 2007-118177 | 5/2007 |
| JP | 2009-504199 | 2/2009 |
| JP | 2010-36285 | 2/2010 |
| JP | 2011-224663 | 11/2011 |
| WO | WO 2014/065196 | 5/2014 |

OTHER PUBLICATIONS

Shibuya Hoppmann: "Dual-Arm Robots", Jun. 2, 2011, Retrieved from the Internet: URL:http://www.youtube.com/watch?v=cW7UhwCmAc, XP054975348.

Extended European Search Report for corresponding EP Application No. 13198521.0-1712, Mar. 17, 2014.

Japanese Office Action for corresponding JP Application No. 2012-278569, Jun. 3, 2014.

Chinese Office Action for corresponding CN Application No. 201310712269.8, May 5, 2015.

Japanese Office Action for corresponding JP Application No. 2012-278569, Jan. 27, 2015.

* cited by examiner

AUTOMATIC PREPARATION SYSTEM

CROSS-REFERENCE TO RELATED APPLICATION

This application is based upon and claims the benefit of priority from the prior Japanese Patent Application No. 2012-278569, filed on Dec. 20, 2012, the entire contents of which are incorporated by reference.

FIELD

The embodiment discussed herein is directed to an automatic preparation system.

BACKGROUND

Japanese Patent Application Laid-open No. 2003-269763 discloses a safety cabinet that includes a case having a workspace inside thereof, a door capable of opening/closing an opening provided on a wall surface of the case, and a suction unit connected to the case for sucking the air inside the case.

SUMMARY

An automatic preparation system according to an aspect of an embodiment includes a case, a pressure regulator, and a plurality of robots. The case has a workspace inside thereof. The pressure regulator keeps a negative pressure inside the case relative to the outside. The robots are installed on a ceiling surface of the case and have respective arms. The robots bring the arms into cooperation to perform a preparation operation.

BRIEF DESCRIPTION OF DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF EMBODIMENT

Figure 1A:
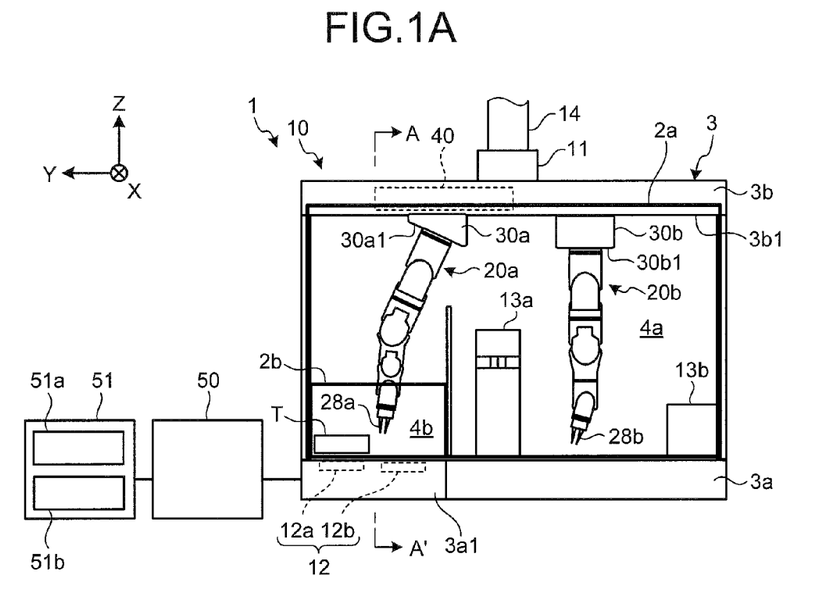
FIGS. 1A, 1B, and 1C are illustrations of an automatic preparation system according to an embodiment.
Figure 1B:
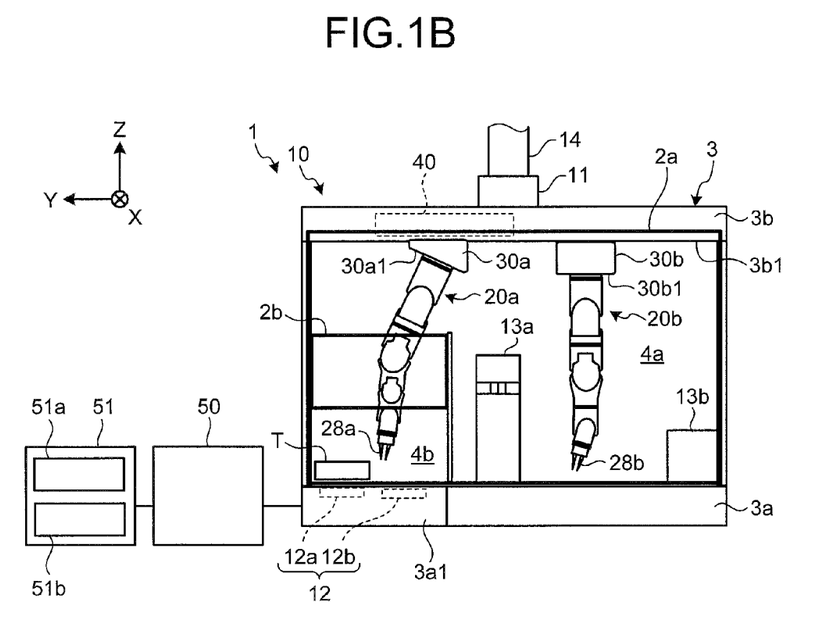
Figure 1C:
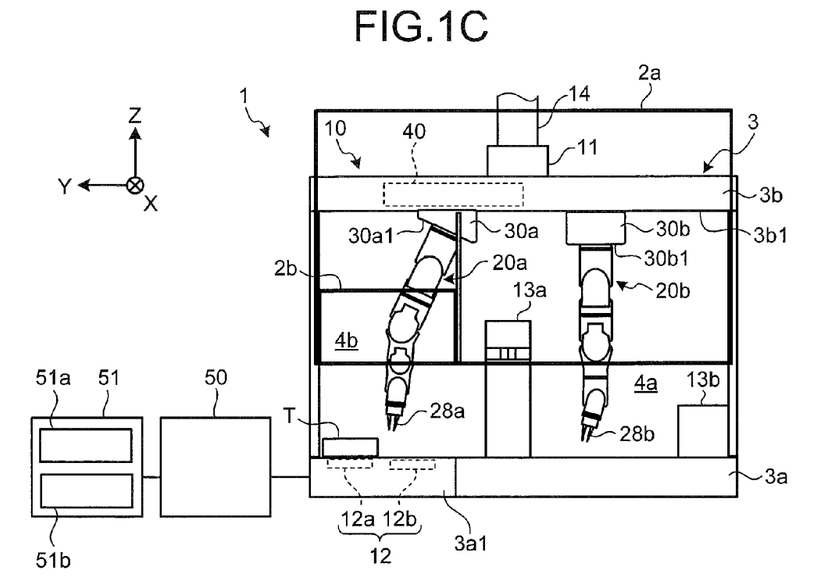

FIGS. 1A, 1B, and 10 are illustrations of an automatic preparation system 1 according to an embodiment.

FIG. 1A illustrates a state in which doors 2a and 2b close openings 4a and 4b of a case 3. FIG. 1B illustrates a state in which only the opening 4b of the case 3 is opened by the door 2b. FIG. 10 illustrates a state in which the opening 4a of the case 3 is opened by the door 2a.

FIG. 1A to FIG. 10 illustrate a three-dimensional orthogonal coordinate system with the Z axis having a positive direction in the vertically upward direction and a negative direction in the vertically downward direction, the X axis in the front-back direction of the case 3, and the Y axis in the left-right direction, for the sake of easy explanation. This orthogonal coordinate system may also be illustrated in the other drawings to be used in the description later.

As illustrated in FIG. 1A to FIG. 10, the automatic preparation system 1 includes a safety cabinet 10, a plurality of robots 20a and 20b, a controller 50, and a simulator 51.

In the automatic preparation system 1, when a tray T that accommodates a drug container having a drug before preparation sealed therein is carried into the safety cabinet 10 by a carrier described later, the robots 20a and 20b perform an operation of preparing a drug in the safety cabinet 10. The automatic preparation system 1 then carries the tray T accommodating the drug after preparation out of the safety cabinet 10, with the carrier.

As described above, the automatic preparation system 1 is a system that automates a drug preparation operation. Although the robots 20a and 20b perform a drug preparation operation in the following description, the automatic preparation system 1 is applicable to operations of the robots 20a and 20b other than a drug preparation operation. Specifically, for example, the automatic preparation system is also applicable to an operation of producing foods or industrial products by blending liquid, gaseous, or powdery materials.

Components of the automatic preparation system 1 will be described below. The safety cabinet 10 includes a case 3, doors 2a and 2b, a suction unit (pressure regulator) 11, and a carrier 12.

The case 3 is an approximately rectangular parallelepiped-shaped metal box and has a workspace inside thereof. The material and shape of the case 3 are not limited to those described above and may be changed appropriately depending on the contents of preparation operations.

Figure 2:
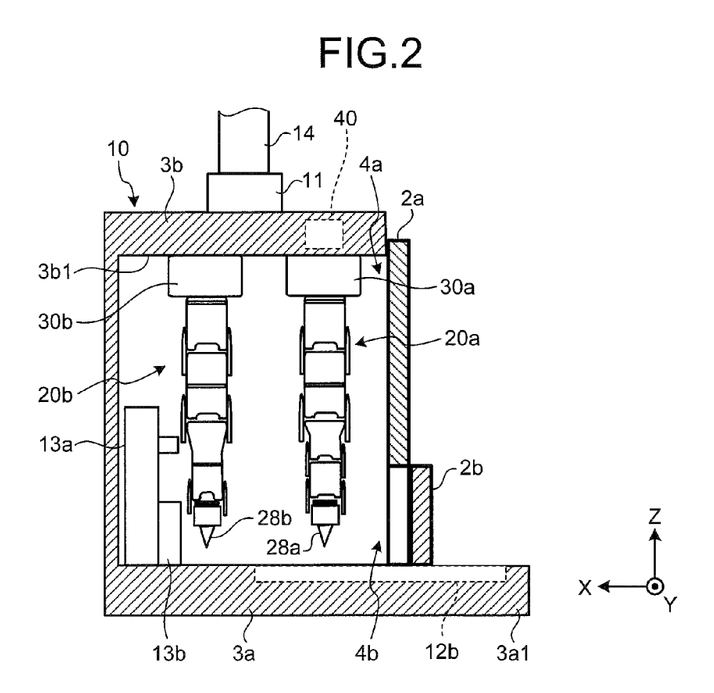
FIG. 2 is a cross-sectional view along A-A' in FIG. 1A.

FIG. 2 is a cross-sectional view along A-A' in FIG. 1A. As illustrated in FIG. 2, the opening 4a that communicates the internal space with the external space is provided in one of four wall surfaces at the front, back, left, and right of the case 3, for example, on the front surface side (the right side in FIG. 2). The opening 4a is formed in an approximately rectangular shape over the entire front surface side of the case 3. The door 2a capable of opening/closing the opening 4a is attached to the case 3.

As is clearly illustrated in FIG. 1B and FIG. 2, the opening 4b is provided in the door 2a. Specifically, for example, in FIG. 1B, the lower left portion of the door 2a is partially cut out in an approximately rectangular shape to form the opening 4b. The door 2b capable of opening/closing the opening 4b is attached to the case 3 so as to overlap the door 2a on the outside. This opening 4b is used to carry drugs in/out as described later. As described above, the opening 4b for carry-in/out is provided at a place where drugs are carried in/out on the wall surface side of the case 3. The opening 4b is arranged in the vicinity of the robot 20a, which will be described later.

The two doors 2a and 2b are formed with, for example, metal guide rails and a tempered glass fitted in the guide rails and having such a light-transmittance that enables the inside of the doors 2a and 2b to be seen through from the outside of the doors 2a and 2b.

These doors 2a and 2b each are configured to be able to move up/down. As illustrated in FIG. 1A, the openings 4a and 4b are closed by lowering both of the doors 2a and 2b to provide a closed space in which the inside of the case 3 is isolated from the outside. The opening 4b is opened by elevating only the door 2b as illustrated in FIG. 1B. The opening 4a is opened by elevating the door 2a as illustrated in FIG. 10.

When the doors 2a and 2b are in the state as illustrated in FIG. 1A, the automatic preparation system 1 causes the robots 20a and 20b arranged inside the case 3 to cooperate to perform a drug preparation operation, thereby reliably protecting the operator from toxic substances, which will be detailed later.

When the doors 2a and 2b are in the state illustrated in FIG. 1B, for example, the automatic preparation system 1 can cause the carrier 12 to carry drugs in/out. Thus, the area in which the internal space of the case 3 is in communication with the external space can be reduced when a drug is carried in/out, and the time required for carry-in/out can also be reduced, thereby protecting the operator from toxic substances even more reliably, which will also be described later.

Furthermore, in the automatic preparation system 1, the doors 2a and 2b are brought into the state illustrated in FIG. 10 to widely open the front surface side of the case 3, whereby, for example, a maintenance operation for robots 20a and 20b can be readily performed.

The bottom 3a of the case 3 functions as a workbench, on which a variety of tools for use in a drug preparation operation are placed. The tools for the preparation operation are, for example, a holder 13a for temporarily holding a syringe S described later and a waste bottle 13b into which the used syringe S is disposed of. In addition to the holder 13a and the waste bottle 13b, for example, a temporary workbench on which a drug container (vial) V filled with a drug is temporarily put is placed on the bottom 3a, although not illustrated in the drawings for the sake of brevity. The holder 13a and the waste bottle 13b are schematically depicted as they are not the main features of the present embodiment.

Figure 3:
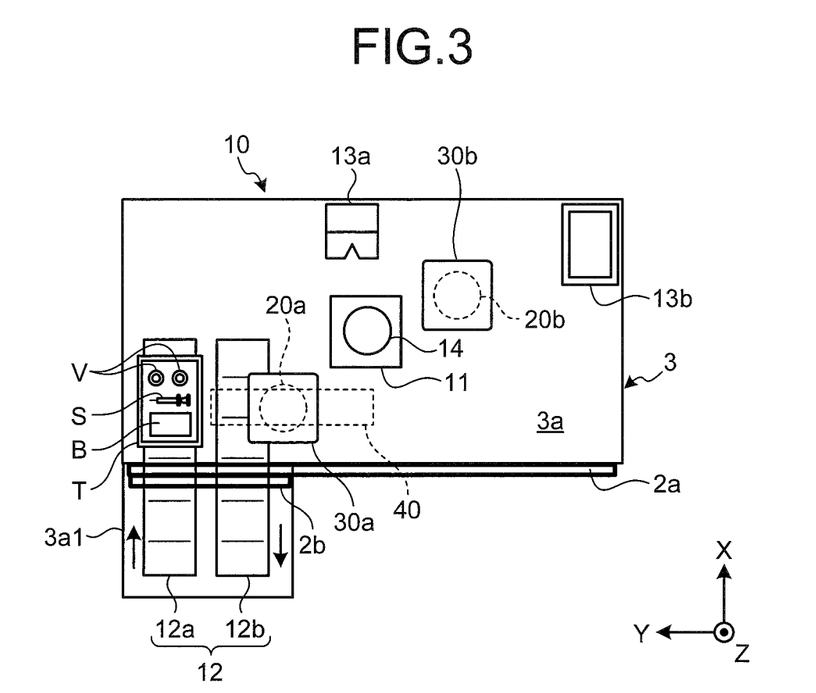
FIG. 3 is a plan view illustrating a safety cabinet illustrated in FIG. 1A.

FIG. 3 is a plan view illustrating the safety cabinet 10. FIG. 3 illustrates a ceiling 3b of the case 3 in a see-through view for the sake of easy understanding of the shape of the bottom 3a of the case 3 and the arrangement of the carrier 12, the robots 20a and 20b, and the like.

As is clearly illustrated in FIG. 3, a protrusion 3a1 protruding outward is formed at the bottom 3a of the case 3. Specifically, for example, the protrusion 3a1 is formed so as to partially protrude from the lower left portion in FIG. 3 of the bottom 3a in the negative direction of the X-axis. The carrier 12 for carrying drugs into/out of the case 3 is installed on the protrusion 3a1.

The carrier 12 includes a plurality of conveyors. Specifically, the carrier 12 includes a first conveyor 12a and a second conveyor 12b. The first and the second conveyors 12a and 12b each are a belt conveyor that drives a belt with a not-illustrated drive source (for example, a servomotor). The first and the second conveyors 12a and 12b are not limited to belt conveyors but may be roller conveyors, chain conveyors, or any other carriers.

The first and the second conveyors 12a and 12b are arranged in parallel (approximately parallel) with the X axis. Both conveyers have one end in the longitudinal direction located in the protrusion 3a1, that is, outside the case 3, and have the other end arranged so as to be located inside the case 3.

The first and the second conveyors 12a and 12b are configured such that the driving directions of the belts are opposite to each other. That is, the belt of the first conveyor 12a is driven from the outside of the case 3 toward the inside, in other words, in the positive direction of the X axis. The belt of the second conveyor 12b is driven from the inside of the case 3 toward the outside, in other words, in the negative direction of the X axis.

The operator therefore can perform an operation of carrying a drug into/out of the case 3 through the carrier 12. That is, the operator puts a tray T accommodating objects required for a preparation operation, such as a drug container V having a drug before preparation sealed therein, a syringe S, and an infusion bag B, on the first conveyor 12a of the protrusion 3a1. The first conveyor 12a is then driven to carry the tray T into the case 3 while the opening 4b of the case 3 is open. FIG. 3 illustrates a state in which the tray T is carried in.

Although not illustrated, the tray T accommodating the infusion bag B having a drug after preparation sealed therein is put onto the second conveyor 12b in the case 3 by the robots 20a and 20b, as described later. The second conveyor 12b is then driven to carry the tray T from the inside of the case 3 to the outside, to be precise, to the protrusion 3a1 while the opening 4b of the case 3 is open. The carrier 12 and the opening 4b correspond to means for carrying in/out drugs to be used in a preparation operation in the case 3.

As described above, the automatic preparation system 1 provided with the carrier 12 enables the operator to perform a drug carry-in/out operation without inserting his/her hands into the case 3, thereby protecting the operator from toxic substances more reliably.

The driving directions of the conveyors 12a and 12b are illustrated only by way of example and may be opposite. The carrier 12 includes two conveyors 12a and 12b in the foregoing description. However, the embodiment is not limited thereto. For example, the carrier 12 may include one conveyor, and a motor serving as a drive source may be driven in the forward or backward direction to switch the driving directions of the belt.

As is clearly illustrated in FIG. 1A or other drawings, for example, the suction unit 11 is a fan provided on the ceiling 3b of the case 3 for sucking the air inside the case 3 to regulate the pressure. The suction unit 11 includes a high efficiency particulate air filter (HEPA) for purifying the air sucked from the inside of the case 3 and discharges the air purified by the HEPA filter to the outdoors through an exhaust dust 14. Accordingly, the workspace inside the case 3 is kept at a negative pressure relative to the outside of the case 3, so that toxic substances and the like produced during the operation are not diffused to the outside. As described above, the suction unit 11 corresponds to means for keeping a negative pressure inside the case 3 relative to the outside.

The number of robots 20a and 20b is two, for example. The number of robots is not limited to two but may be three or more. In the following, the robot denoted by the reference sign 20a in FIG. 1A is referred to as the "first robot" (corresponding to one robot), and the robot denoted by the reference sign 20b is referred to as the "second robot" (corresponding to the other robot).

The first and the second robots 20a and 20b are ceiling-suspended multi-axis robots installed on a ceiling surface 3b1 of the case 3. Specifically, the first robot 20a is attached to a first base 30a and installed on the ceiling surface 3b1 with the first base 30a interposed therebetween. Similar to the first robot 20a, the second robot 20b is attached to a second base 30b and is installed on the ceiling surface 3b1 with the second base 30b interposed therebetween.

End effectors 28a and 28b are connected to the front ends of the first and the second robots 20a and 20b, respectively. The end effectors 28a and 28b are robot hands capable of gripping a drug container V and a syringe S for example. The end effectors 28a and 28b are not limited to robot hands but may be suction units that suck and hold a drug container V and the like as long as they can perform a preparation operation.

Figure 4:
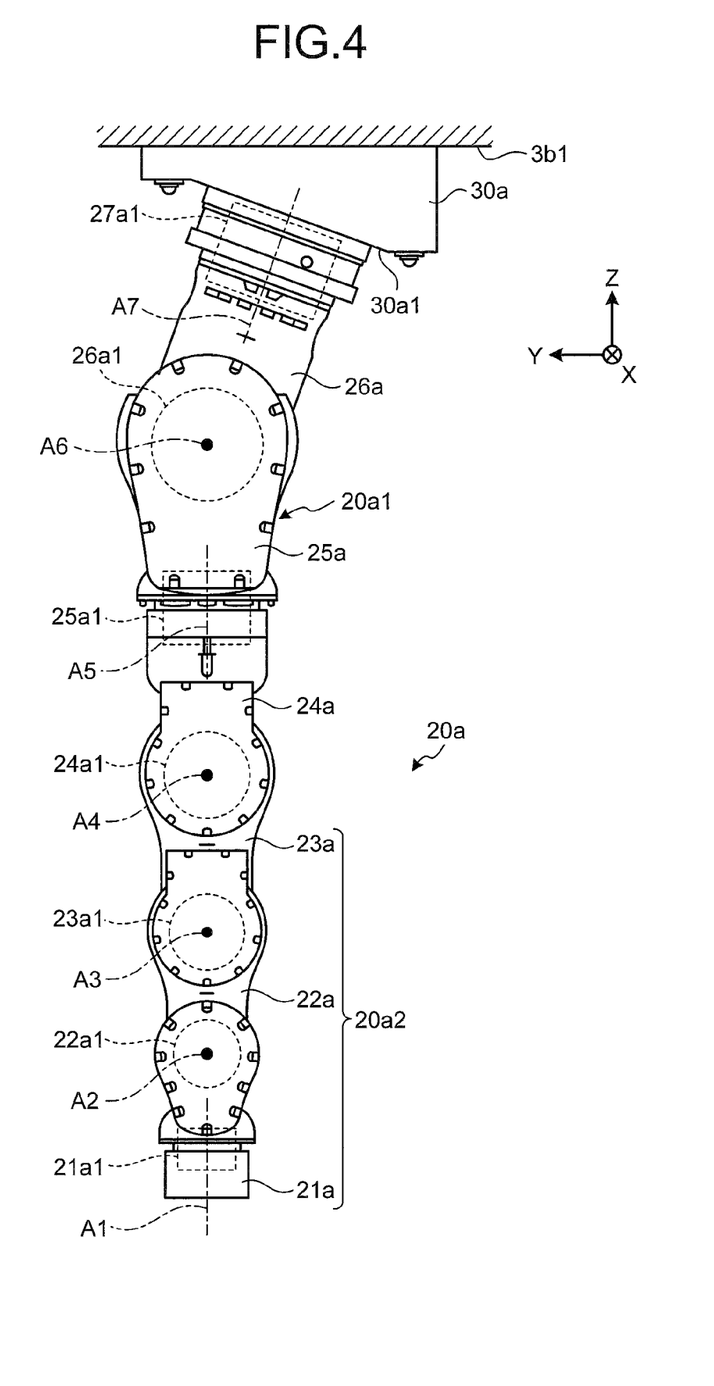
FIG. 4 is a front view illustrating a configuration of a first robot illustrated in FIG. 1A.

FIG. 4 is a front view illustrating a configuration of the first robot 20a illustrated in FIG. 1A.

As illustrated in FIG. 4, the first robot 20a is a seven-axis robot having an arm 20a1. Specifically, the first robot 20a includes a first arm portion 21a to a sixth arm portion 26a, and the end effector 28a (not illustrated in FIG. 4) connected to the first arm portion 21a.

The first arm portion 21a (corresponding to the first one-side arm portion) has a base end supported by the second arm portion 22a (corresponding to the second one-side arm portion) and has a front end supporting the end effector 28a. The second arm portion 22a has a base end supported by the third arm portion 23a (corresponding to the third one-side arm portion) and has a front end supporting the first arm portion 21a. The third arm portion 23a has a base end supported by the fourth arm portion 24a and has a front end supporting the second arm portion 22a.

As described above, the first arm portion 21a provided at the front end of the arm 20a1 and connected to the end effector 28a, and the second and third arm portions 22a and 23a connected to the first arm portion 21a are referred to as a "wrist mechanism" in the specification and denoted by a reference sign 20a2 in FIG. 4.

The fourth arm portion 24a has a base end supported by the fifth arm portion 25a and has a front end supporting the third arm portion 23a. The fifth arm portion 25a has a base end supported by the sixth arm portion 26a and has a front end supporting the fourth arm portion 24a. The sixth arm portion 26a has a base end supported by the first base 30a and has a front end supporting the fifth arm portion 25a.

The first robot 20a includes a first actuator 21a1 to a seventh actuator 27a1 at joints by which the first arm portion 21a to the sixth arm portion 26a and the first base 30a are coupled.

Specifically, the end effector 28a (not illustrated in FIG. 4) is coupled with the first arm portion 21a through the first actuator 21a1. The driving of the first actuator 21a1 rotates the end effector 28a about a rotation axis A1 (corresponding to the first one-side rotation axis and hereinafter referred to as the "first rotation axis A1") of the first actuator 21a1.

The first arm portion 21a is coupled with the second arm portion 22a through the second actuator 22a1. The driving of the second actuator 22a1 rotates the first arm portion 21a about a rotation axis A2 (corresponding to the second one-side rotation axis and hereinafter referred to as the "second rotation axis A2") of the second actuator 22a1. The second arm portion 22a is coupled with the third arm portion 23a through the third actuator 23a1. The driving of the third actuator 23a1 rotates the second arm portion 22a about a rotation axis A3 (corresponding to the third one-side rotation axis and hereinafter referred to as the "third rotation axis A3") of the third actuator 23a1.

The third arm portion 23a is coupled with the fourth arm portion 24a through the fourth actuator 24a1. The driving of the fourth actuator 24a1 rotates the third arm portion 23a about a rotation axis A4 (hereinafter referred to as the "fourth rotation axis A4") of the fourth actuator 24a1. The fourth arm portion 24a is coupled with the fifth arm portion 25a through the fifth actuator 25a1. The driving of the fifth actuator 25a1 rotates the fourth arm portion 24a about a rotation axis A5 (hereinafter referred to as the "fifth rotation axis A5") of the fifth actuator 25a1.

The fifth arm portion 25a is coupled with the sixth arm portion 26a through the sixth actuator 26a1. The driving of the sixth actuator 26a1 rotates the fifth arm portion 25a about a rotation axis A6 (hereinafter referred to as the "sixth rotation axis A6") of the sixth actuator 26a1. The sixth arm portion 26a is coupled with the first base 30a through the seventh actuator 27a1. The driving of the seventh actuator 27a1 rotates the sixth arm portion 26a to rotate about a rotation axis A7 (hereinafter referred to as the "seventh rotation axis A7") of the seventh actuator 27a1.

In the wrist mechanism 20a2 of the first robot 20a, the first rotation axis A1 is perpendicular (at right angles) to the second rotation axis A2, and the second rotation axis A2 is perpendicular to the first rotation axis A1 and parallel to the third rotation axis A3. In the wrist mechanism 20a2, the third rotation axis A3 is parallel to the second rotation axis A2 and the fourth rotation axis A4.

The fourth rotation axis A4 is parallel to the third rotation axis A3 and perpendicular to the fifth rotation axis A5. The fifth rotation axis A5 is perpendicular to the fourth rotation axis A4 and the sixth rotation axis A6. The sixth rotation axis A6 is perpendicular to the fifth rotation axis A5 and the seventh rotation axis A7. The seventh rotation axis A7 is perpendicular to the sixth rotation axis A6. The words such as "perpendicular" and "parallel" referred to herein do not necessarily require mathematical precision and permit substantial tolerances or errors.

In the first robot 20a, the arrangement of the rotation axes A1, A2, and A3 in the wrist mechanism 20a2 is configured as described above, thereby facilitating the bend of the wrist portion and achieving a structure suitable for performing an operation, such as lifting the tray T.

For example, as illustrated in FIG. 1A, the above-noted opening 4b is provided in the vicinity of the first robot 20a having the structure described above. The first robot 20a thus can readily perform a drug carry-in/out operation. That is, the first robot 20a can readily perform an operation such as lifting the tray T carried in from the opening 4b because the first robot 20a and the opening 4b are in proximity to each other.

Figure 5:
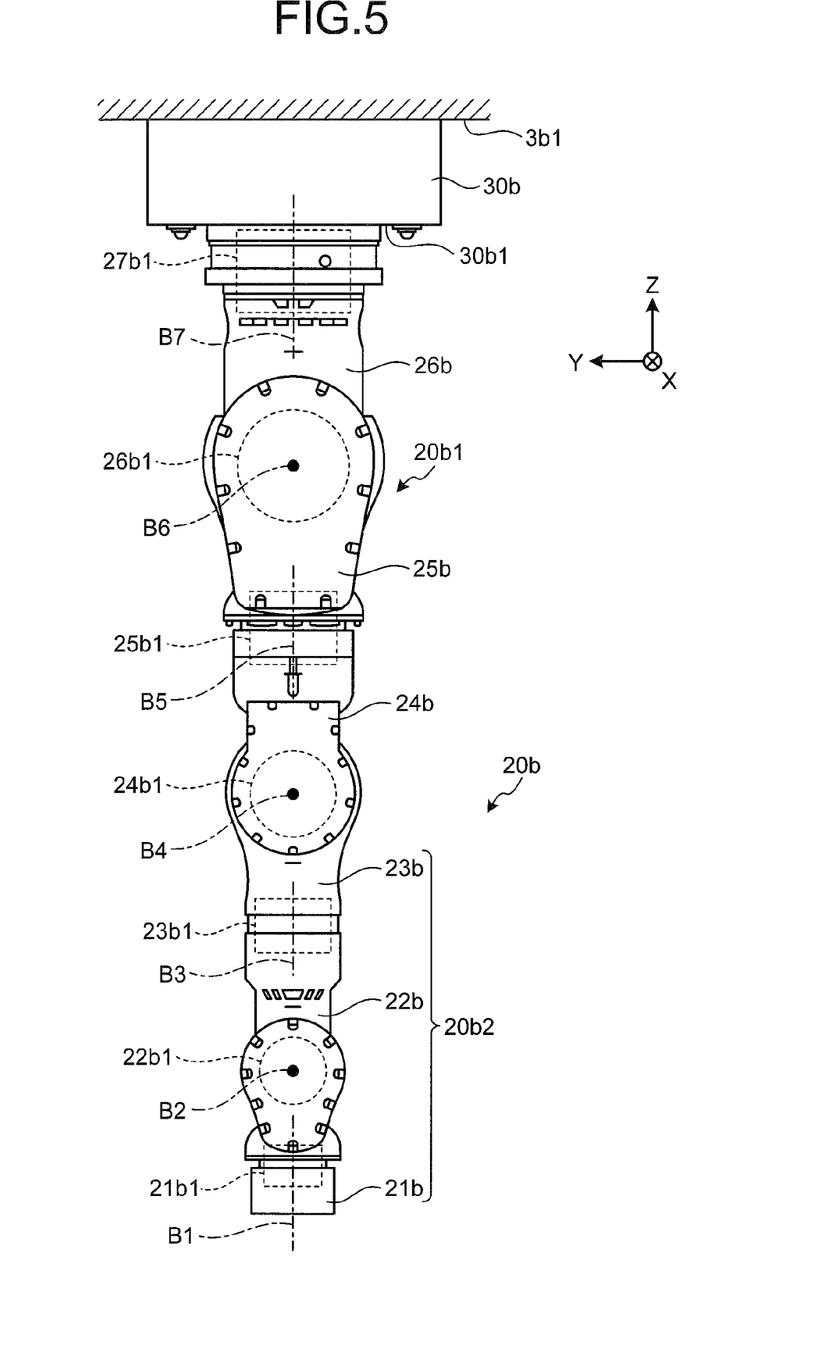
FIG. 5 is a front view illustrating a configuration of a second robot illustrated in FIG. 1A.

FIG. 5 is a front view similar to FIG. 4, illustrating a configuration of the second robot 20b.

The second robot 20b is a seven-axis robot similar to the first robot 20a, having an arm 20b1. The second robot 20b is the same as the first robot 20a in that it includes a first arm portion 21b to a sixth arm portion 26b and a first actuator 21b1 to a seventh actuator 27b1. However, the wrist mechanism 20b2 of the second robot 20b differs from the wrist mechanism 20a2 of the first robot 20a. In the specification, the "wrist mechanism 20b2 of the second robot 20b" means the first arm portion 21b to third arm portion 23b, in the same manner as in the wrist mechanism 20a2 of the first robot 20a.

Specifically, in the wrist mechanism 20b2 of the second robot 20b, a first rotation axis B1 (corresponding to the first other-side rotation axis) of the first actuator 21b1 driving the end effector 28b (not illustrated in FIG. 5) is perpendicular to a second rotation axis B2 (corresponding to the second other-side rotation axis) of the second actuator 22b1 driving the first arm portion 21b (corresponding to the first other-side arm portion). The second rotation axis B2 is perpendicular to the first rotation axis B1 and a third rotation axis B3 (corresponding to the third other-side rotation axis) of the third actuator 23b1 driving the second arm portion 22b (corresponding to the second other-side arm portion). The third rotation axis B3 is perpendicular to the second rotation axis B2 and a fourth rotation axis B4 of the fourth actuator 24a1 driving the third arm portion 23b (corresponding to the third other-side arm portion).

In the second robot 20b, the arrangement of the rotation axes B1, B2, and B3 in the wrist mechanism 20b2 is configured as described above, thereby facilitating rotation of the wrist portion and achieving a structure suitable for performing an operation, such as gripping the syringe S and stirring the sealed drug.

Figure 6A:
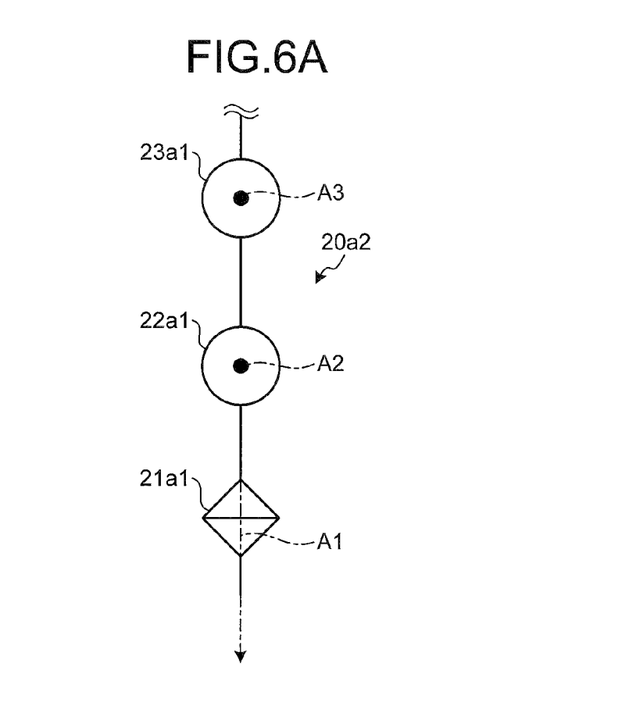
FIG. 6A is an illustration of a wrist mechanism of the first robot illustrated in FIG. 1A.
Figure 6B:
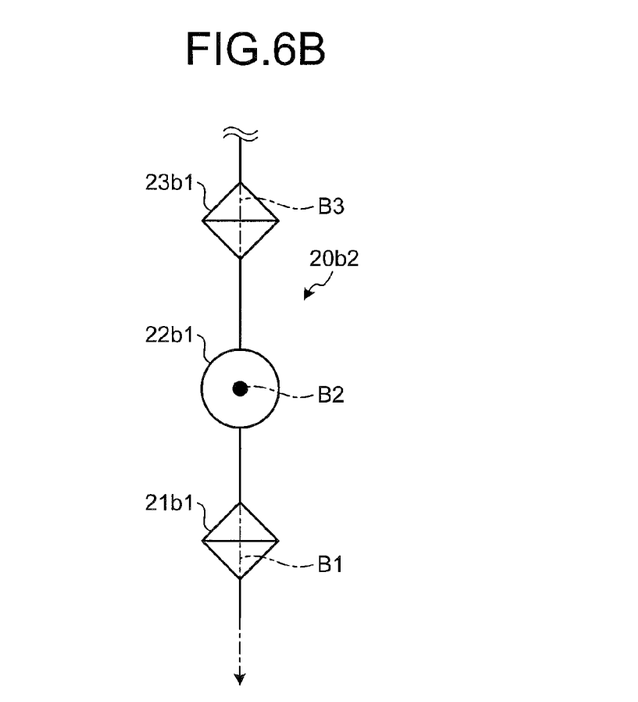
FIG. 6B is an illustration of a wrist mechanism of the second robot illustrated in FIG. 1A.

FIG. 6A is an illustration of the wrist mechanism 20a2 of the first robot 20a, and FIG. 6B is an illustration of the wrist mechanism 20b2 of the second robot 20b. As illustrated in FIG. 6A and FIG. 6B, the wrist mechanism 20a2 of the first robot 20a and the wrist mechanism 20b2 of the second robot 20b are differentiated as described above. Specifically, the orientation of the third rotation axis A3 of the first robot 20a is differentiated from the orientation of the third rotation axis B3 of the second robot 20b. Accordingly, operations to which the first robot 20a is dedicated can be made different from that of the second robot 20b, so that the robots 20a and 20b can cooperate efficiently. As a result, the drug preparation operation can be performed promptly.

The attitude at which the first robot 20a reaches a singularity and the attitude at which the second robot 20b reaches a singularity can be made different because the wrist mechanism 20a2 differ from the wrist mechanism 20b2. Specifically, there is a position (attitude) called a singularity in an articulated robot having a plurality of joint axes. Specifically, a singularity refers to a position at which solutions to the inverse kinematics calculation for determining the angle of each joint axis from the position and attitude of the robot front end are indefinite. When the robot reaches a singular configuration, a command value to the motor for driving each joint axis cannot be determined, and the robot cannot be brought into motion.

The singular configuration can be differentiated between the first robot 20a and the second robot 20b whereby, in the cooperation between the first and the second robots 20a and 20b, the operation that brings one robot into the singular configuration can be performed instead by the other robot. With this configuration, the preparation operation can be performed while preventing the first robot 20a and the second robot 20b from reaching the singular configuration.

The first and the second bases 30a and 30b will now be described. As is clearly illustrated in FIGS. 4 and 5, the angle of an attachment surface 30a1 of the first base 30a to which the first robot 20a is attached, with respect to the horizontal plane (the X-Y plane), differs from the angle of an attachment surface 30b1 of the second base 30b to which the second robot 20b is attached, with respect to the horizontal plane.

Specifically, for example, the attachment surface 30a1 of the first base 30a is formed so as to be inclined to the horizontal plane at a certain angle, while the attachment surface 30b1 of the second base 30b is approximately parallel to the horizontal plane.

Thus, the motion range of each robot 20a, 20b can be extended, and the preparation operation can be performed while avoiding the singular configuration of the first robot 20a and the second robot 20b.

That is, the respective motion ranges of the robots 20a and 20b can be made different because the angles of the attachment surfaces 30a1 and 30b1 of the first and second bases 30a and 30b are differentiated from each other as described above, whereby, for example, the preparation operation that makes one robot reach the singular configuration can be performed instead by the other robot. With this configuration, the preparation operation can be executed reliably while avoiding the singular configuration of the first robot 20a and the second robot 20b.

The attachment surface 30a1 of the first base 30a is inclined so as to face the carry-in/out port for drugs, that is, the opening 4b of the case 3, as illustrated, for example, in FIG. 1A. Therefore, in the first robot 20a, when compared with a case where the attachment surface is oriented horizontally, the end effector 28a can be driven to the neighborhood of the place where the tray T is arranged (specifically, the carrier 12), without excessively flexing the joints that are the coupling portions. This makes a prompt preparation operation.

The inclination of the attachment surface 30a1 of the first base 30a can prevent the first robot 20a from reaching the singular configuration in the possible attitudes from the carry-in operation through the preparation operation to the carry-out operation.

As illustrated, for example, in FIG. 1A, at least one of the first and the second robots 20a and 20b, specifically, the first robot 20a is connected to a slide mechanism 40 for sliding the first robot 20a on the ceiling surface 3b1 of the case 3.

The slide mechanism 40 includes, for example, a servomotor and a ball screw, although not illustrated. The ball screw includes a threaded shaft, a nut (slider), and a ball. The nut is screwed onto the threaded shaft with the ball interposed therebetween. The first base 30a of the first robot 20a is attached to the nut. The output shaft of the servomotor is connected to one end of the threaded shaft. Thus, the servomotor rotates the threaded shaft, causing the first robot 20a attached to the nut (slider) and the first base 30a to slide (horizontally move) on the ceiling surface 3b1, in other words, linearly move in the Y-axis direction.

As described above, the provision of the slide mechanism 40 extends the motion range of the first robot 20a and makes a more prompt preparation operation. The slide mechanism 40 is not limited to the configuration using the ball screw described above but may be such a configuration that drives a link mechanism with a motor and moves the slider by the driving of the link mechanism.

The above-noted opening 4b is provided in the vicinity of the first robot 20a provided with the slide mechanism 40. Accordingly, the first robot 20a can reduce the time required for the drug carry-in/out operation. That is, the first robot 20a can move to the neighborhood of the opening 4b with the slide mechanism 40, lift the tray T carried in from the opening 4b, and then return to the operation position with the slide mechanism 40, thereby reducing the time for the drug carry-in/out operation.

The first robot 20a and the second robot 20b are arranged to be spaced apart from each other by a certain distance in the Y-axis direction. As is clearly illustrated in FIG. 3, the first robot 20a is arranged so as to be shifted from the second robot 20b in the X-axis direction. Specifically, for example, the first robot 20a is arranged on the front surface side of the case 3, while the second robot 20b is arranged on the back surface side of the case 3.

Thus, the motion range of the arm 20a1 of the first robot 20a and the motion range of the arm 20b1 of the second robot 20b can be shifted from each other, whereby the workspace inside the case 3 can be efficiently used.

The suction unit 11 is installed between the first robot 20a and the second robot 20b on the ceiling surface 3b1. Thus, toxic substances in the case 3 can be efficiently discharged to the outdoors. That is, the drug is arranged between the first and the second robots 20a and 20b for a longer time because the preparation operation is performed by cooperation between the first and the second robots 20a and 20b. Therefore, the installation of the suction unit 11 at the position described above enables toxic substances produced from the drug present between the first and the second robots 20a and 20b to be discharged efficiently from the suction unit 11 to the outdoors.

The first and the second robots 20a and 20b, the carrier 12, the slide mechanism 40, and other units are connected to the controller 50 provided outside of the case 3 so that the controller 50 controls the motions thereof.

The controller 50 is connected to, for example, the simulator 51 that simulates the operation of the first and the second robots 20a and 20b to perform a predetermined motion. The controller 50 accepts teaching data for teaching the first and the second robots 20a and 20b a predetermined motion from the simulator 51 and controls the motions of the robots 20a and 20b based on the accepted teaching data.

The simulator 51 is configured with a processor (for example, a personal computer or a programming pendant) having a display screen 51a and an input device 51b and is connected to the controller 50 to be able to transmit/receive data. The display screen 51a displays a schematic diagram of the inside of the case 3 as viewed from above for example. Although the simulator 51 is provided in the foregoing explanation, the embodiment is not limited thereto. For example, the simulator 51 may be removed, and a predetermined motion may be stored (taught) in the controller 50 in advance.

Figure 7:
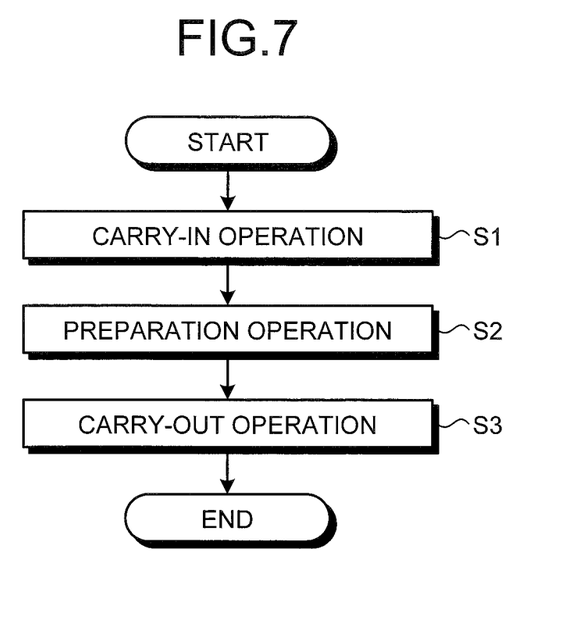
FIG. 7 is a flowchart illustrating a procedure of operations performed in the automatic preparation system according to the embodiment.

The flow of operations performed by the automatic preparation system 1 will now be described with reference to FIG. 7. FIG. 7 is a flowchart illustrating a process procedure of a series of preparation operations performed in the automatic preparation system 1. The automatic preparation system 1 executes each operation illustrated in FIG. 7 under the control of the controller 50, to which the operator inputs a process procedure through the simulator 51.

As illustrated in FIG. 7, in the automatic preparation system 1, a carry-in operation is performed, in which a tray T that accommodates a vessel such as a drug container V having a drug before preparation sealed therein is carried into the case 3 (step S1). It is assumed that a drug container V, a syringe S, and an infusion bag B are set at certain positions on the tray T.

In the carry-in operation, the operator sets the tray T on the first conveyor 12a. The controller 50 then elevates the door 2b to open the opening 4b and then drives the first conveyor 12a to carry the tray T into the case 3. The door 2b is then lowered to close the opening 4b.

The automatic preparation system 1 then performs a preparation operation of preparing a drug (step S2). In the preparation operation, for example, the controller 50 causes the first robot 20a to move to the vicinity of the tray T with the slide mechanism 40 and to grip and lift the tray T with the end effector 28a. The first robot 20a is thereafter moved with the slide mechanism 40 to the neighborhood of the center of the case 3, where the tray T is placed on the operation position. As described above, the first robot 20a having a structure suitable for performing the lifting operation carries the tray T to the operation position, thereby making a prompt preparation operation.

The controller 50 performs a drug preparation operation by bringing the arm 20a1 of the first robot 20a and the arm 20b1 of the second robot 20b into cooperation. For example, the first robot 20a sets the syringe S in the holder 13a. The second robot 20b grips the drug container V and sticks the needle of the syringe S set in the holder 13a into the drug container V. The first robot 20a then pulls the plunger of the syringe S to take up a certain amount of the drug in the drug container V into the syringe S. As described above, the controller 50 corresponds to means for making the robots 20a and 20b bring the arms 20a1 and 20b1 into cooperation to perform the preparation operation.

The second robot 20b then removes the syringe S from the holder 13a and returns the syringe S to the holder 13a after stirring. The second robot 20b grips the infusion bag B. The infusion bag B contains therein an infusion product, such as physiological saline solution and glucose. The second robot 20b sticks the needle of the syringe S into the infusion bag B at an appropriate position. The first robot 20a pushes the plunger of the syringe S and injects the drug in the syringe S into the infusion bag B. The first robot 20a then returns the infusion bag B to the tray T. The second robot 20b disposes of the used drug container V and syringe S into the waste bottle 13b.

The automatic preparation system 1 then performs an operation of carrying out (ejecting) the drug after preparation (step S3). In this carry-out operation, for example, the first robot 20a, gripping and lifting the tray T, is moved to the vicinity of the second conveyor 12b with the slide mechanism 40. The first robot 20a then places the tray T on the second conveyor 12b.

The controller 50 elevates the door 2b to open the opening 4b and then drives the second conveyor 12b to carry the tray T out of the case 3. The door 2b is then lowered to close the opening 4b. A series of operations is thus completed. The preparation operation described above is illustrated only by way of example, and the embodiment is not limited thereto.

As described above, in the automatic preparation system 1, when a drug is carried in/out, the door 2b is opened/closed such that only the opening 4b is opened. Therefore, the area in which the internal space of the case 3 is in communication with the external space can be reduced, and the time required for carry-in/out can be reduced, thereby protecting the operator from toxic substances more reliably.

As described above, in the automatic preparation system 1 in the present embodiment, the first and the second robots 20a and 20b perform a preparation operation in the inside of the case 3, instead of the operator, so that the operator can be protected even more reliably from toxic substances produced during the operation.

In the automatic preparation system 1, the work area on the bottom 3a can be utilized to its maximum because the first and the second robots 20a and 20b are installed on the ceiling surface 3b1 of the case 3. In addition, the automatic preparation system 1 can be reduced in size, thereby reducing the space required for installation of the automatic preparation system 1.

In the forgoing embodiment, the attachment surface 30a1 of the first base 30a is inclined to the horizontal plane at a certain angle, while the attachment surface 30b1 of the second base 30b is approximately parallel to the horizontal plane. However, the embodiment is not limited thereto. Specifically, as long as the angle of the attachment surface 30a1 of the first base 30a differs from the angle of the attachment surface 30b1 of the second base 30b, for example, both of the attachment surfaces 30a1 and 30b1 may be inclined to the horizontal plane at different angles. For example, the attachment surfaces 30a1 and 30b1 may be inclined in the same direction at angles different from each other.

Alternatively, the attachment surface 30a1 and the attachment surface 30b1 may be inclined in different directions at the same inclination angle with respect to the horizontal plane, or both the directions of inclination and the inclination angles may be different from each other.

In the configuration described above, the door 2a is cut out to provide the opening 4b. However, the embodiment is not limited thereto. For example, the opening 4a and the door 2a may be removed, and the opening 4b may be provided on the wall surface side (the front surface side) of the case 3 such that only the carry-in/out place for drugs is open, and the door 2b may be attached to the opening 4b.

In the foregoing embodiment, the seven-axis robots 20a and 20b having the arms 20a1 and 20b1 respectively are provided. However, robots other than the seven-axis robots (for example, may be six-axis robots) or may be robots of any other kinds such as dual-arm robots can be used.

In the embodiment above, a vial is used as the drug container V. The drug container V is not limited to a vial and may be any container that can contain a drug sealed therein, such as an ampule, an infusion bag, or a bottle.

The contents of a series of preparation operations are not limited to those illustrated in the foregoing embodiment. For example, mixing a plurality of liquid drugs or mixing a liquid drug and a powdery drug can be performed. Although the drug after preparation is sealed in an infusion bag B in the foregoing embodiment, the drug after preparation may be sealed in a syringe S, and the syringe S may be carried out (ejected).

Additional advantages and modifications will readily occur to those skilled in the art. Therefore, the invention in its broader aspects is not limited to the specific details and representative embodiment shown and described herein. Accordingly, various modifications may be made without departing from the spirit or scope of the general inventive concept as defined by the appended claims and their equivalents.

What is claimed is:

1. An automatic preparation system comprising:
   a case having a workspace inside thereof;
   a pressure regulator that keeps a negative pressure inside the case relative to outside; and
   two robots installed on a ceiling surface of the case and having respective arms, wherein
   the two robots bring the arms into cooperation to perform a preparation operation,
   an angle of an attachment surface of a first base, to which one of the two robots is attached, with respect to a horizontal plane differs from an angle of an attachment surface of a second base, to which the other robot of the two robots is attached, with respect to the horizontal plane, and
   the attachment surface of the first base is inclined to face an opening for carrying in/out a drug to be used in the preparation operation in the case.

2. The automatic preparation system according to claim 1, further comprising a slide mechanism that slides at least one of the robots on the ceiling surface of the case.

3. The automatic preparation system according to claim 2, wherein the opening for carrying in/out the drug is provided in the vicinity of the robot provided with the slide mechanism.

4. The automatic preparation system according to claim 3, wherein
   a wrist mechanism of one of the two robots differs from a wrist mechanism of the other robot.

5. The automatic preparation system according to claim 4, wherein
   the wrist mechanism of the one robot includes:
      a first one-side arm portion that supports an end effector rotatably about a first one-side rotation axis;
      a second one-side arm portion that supports the first one-side arm portion rotatably about a second one-side rotation axis perpendicular to the first one-side rotation axis; and
      a third one-side arm portion that supports the second one-side arm portion rotatably about a third one-side rotation axis parallel to the second one-side rotation axis, and
   the wrist mechanism of the other robot includes:
      a first other-side arm portion that supports an end effector rotatably about a first other-side rotation axis;
      a second other-side arm portion that supports the first other-side arm portion rotatably about a second other-side rotation axis perpendicular to the first other-side rotation axis; and
      a third other-side arm portion that supports the second other-side arm portion rotatably about a third other-side rotation axis perpendicular to the second other-side rotation axis.

6. The automatic preparation system according to claim 5, wherein the opening for carrying in/out the drug in the case is provided in the vicinity of the one robot.

7. The automatic preparation system according to claim 6, wherein the one robot carries a tray accommodating the drug to a work position.

8. The automatic preparation system according to claim 3, further comprising:
   a door capable of opening/closing the opening for carrying in/out the drug in the case, wherein
   the door is opened/closed when the drug is carried in/out.

9. The automatic preparation system according to claim 2, wherein
   a wrist mechanism of one of the two robots differs from a wrist mechanism of the other robot.

10. The automatic preparation system according to claim 9, wherein
    the wrist mechanism of the one robot includes:
       a first one-side arm portion that supports an end effector rotatably about a first one-side rotation axis;
       a second one-side arm portion that supports the first one-side arm portion rotatably about a second one-side rotation axis perpendicular to the first one-side rotation axis; and
       a third one-side arm portion that supports the second one-side arm portion rotatably about a third one-side rotation axis parallel to the second one-side rotation axis, and
    the wrist mechanism of the other robot includes:
       a first other-side arm portion that supports an end effector rotatably about a first other-side rotation axis;
       a second other-side arm portion that supports the first other-side arm portion rotatably about a second other-side rotation axis perpendicular to the first other-side rotation axis; and
       a third other-side arm portion that supports the second other-side arm portion rotatably about a third other-side rotation axis perpendicular to the second other-side rotation axis.

11. The automatic preparation system according to claim 1, wherein
    a wrist mechanism of one of the two robots differs from a wrist mechanism of the other robot.

12. The automatic preparation system according to claim 11, wherein
    the wrist mechanism of the one robot includes:
       a first one-side arm portion that supports an end effector rotatably about a first one-side rotation axis;
       a second one-side arm portion that supports the first one-side arm portion rotatably about a second one-side rotation axis perpendicular to the first one-side rotation axis; and
       a third one-side arm portion that supports the second one-side arm portion rotatably about a third one-side rotation axis parallel to the second one-side rotation axis, and
    the wrist mechanism of the other robot includes:
       a first other-side arm portion that supports an end effector rotatably about a first other-side rotation axis;

a second other-side arm portion that supports the first other-side arm portion rotatably about a second other-side rotation axis perpendicular to the first other-side rotation axis; and a third other-side arm portion that supports the second other-side arm portion rotatably about a third other-side rotation axis perpendicular to the second other-side rotation axis.

13. The automatic preparation system according to claim 12, wherein the one robot carries a tray accommodating the drug to a work position.

14. The automatic preparation system according to claim 1, further comprising a carrier that carries the drug into/out of the case.

15. The automatic preparation system according to claim 14, wherein
the carrier includes two conveyors each having one end in a longitudinal direction located outside the case and another end located inside the case, and
the two conveyors have belts whose driving directions are different for carry-in and carry-out.

16. The automatic preparation system according to claim 1, wherein the workspace is a closed space isolated from the outside.

17. The automatic preparation system according to claim 1, wherein the pressure regulator is installed between the two robots on the ceiling surface of the case.

18. The automatic preparation system according to claim 1, wherein the attachment surface of the first base is inclined with respect to the horizontal plane, and the attachment surface of the second base is parallel to the horizontal plane.

19. An automatic preparation system comprising:
a case having a workspace inside thereof;
means for keeping a negative pressure inside the case relative to outside;
means for carrying in/out to drug to be used in a preparation operation in the case;
two robots installed on a ceiling surface of the case and having respective arms; and
means for making the two robots bring the arms into cooperation to perform the preparation operation, wherein
an angle of an attachment surface of a first base, to which one of the two robots is attached, with respect a horizontal plane differs from an angle of an attachment surface of a second base, to which the other robot of the two robots is attached, with respect to the horizontal plane, and
the attachment surface of the first base is inclined to face an opening for carrying in/out of drugs in the case.

20. The automatic preparation system according to claim 19, wherein the means for keeping a negative pressure is installed between the two robots on the ceiling surface of the case.

* * * * *